April 25, 1939. J. J. GRULLEMANS Plant Pat. 329
PHLOX
Filed Nov. 5, 1938
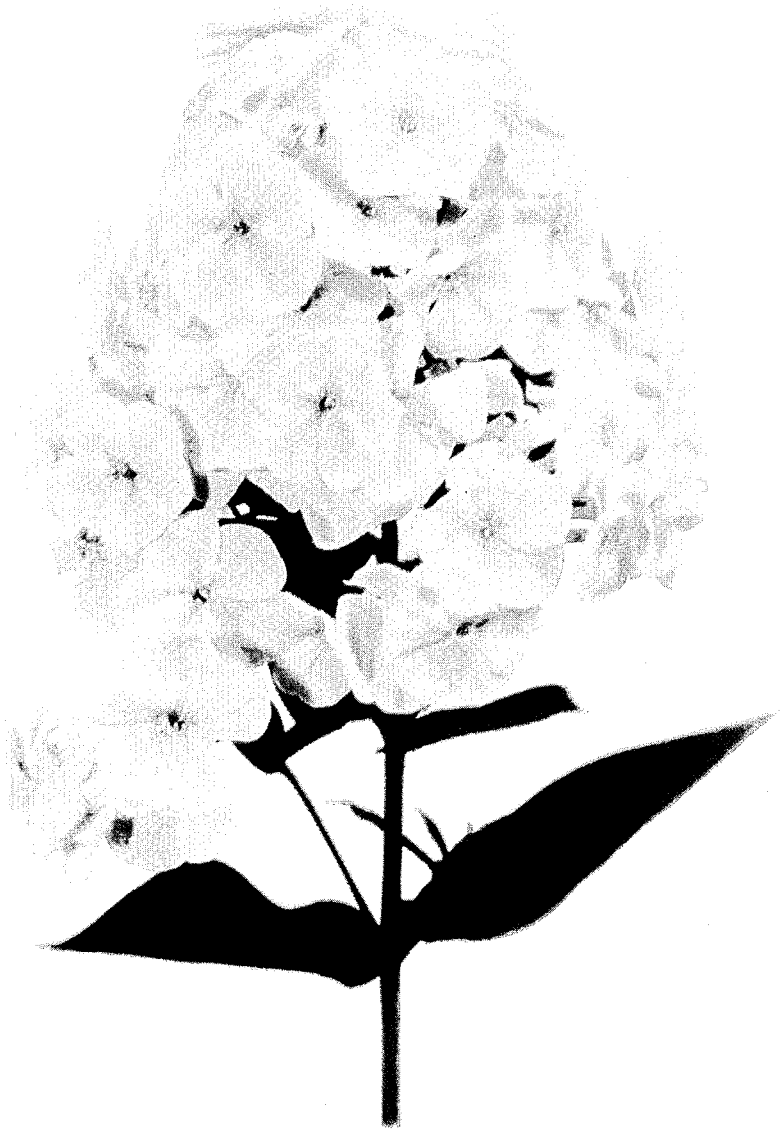
INVENTOR
JOHN J. GRULLEMANS
BY John H. Leonard,
HIS ATTORNEY Patented Apr. 25, 1939

Plant Pat. 329

UNITED STATES PATENT OFFICE

329

PHLOX

John J. Grullemans, Mentor, Ohio, assignor to The Wayside Gardens Company, Mentor, Ohio, a corporation of Ohio Application November 5, 1938, Serial No. 239,074

1 Claim. (Cl. 47—60)

This invention relates to a new variety of phlox produced by crossing the variety "Mia Ruys" as the seed parent with "Antonin Mercier" as the pollen parent. This variety is of the phlox "Decussata" classification. The new variety has been asexually reproduced and each of the reproductions has run true to form.

The plant is compact, vigorous, and has a spreading, bushlike habit and produces eight to ten panicles on a two or three-year-old plant. The stems supporting the bloom heads grow from 24 to 36 inches high, depending upon the soil, although the plant itself is a semi-dwarf. Lateral branches issue from the main stems and bear small flower clusters which prolong the flowering period, this period usually extending throughout the months of July and August.

The foliage is produced in abundance on each of the stems and is of a bottle-green color comparable to Maerz & Paul Plate No. 23 L–12, and it is remarkably resistant to mildew and other foliage diseases.

The bloom heads or panicles of the plant appear as large as seven to eight inches in diameter and eight to nine inches in height. These heads are very compact, with florets or flowers of one-and-one-quarter to two inches in diameter. These individual florets have the quality of lasting for relatively long periods, and they are not damaged materially by rain or sun. The extreme outer portion of each of the florets is white, comparable to Plate No. 2 A-1, having an overcast or hue of blue comparable to Plate No. 41 A–6. The blue appears in a veined manner, especially in the outer portion of the petal adjacent the flower center, and the blue merges into a small, distinct blue eye having a purplish tone comparable to Plate No. 52 K–6. From a distance, the panicle or bloom head gives an appearance of an eggshell white, which is comparable to Plate No. 3 A–1. Generally, the florets last from three to five weeks, this, of course, depending upon weather conditions. In cases where the plant is grown in shade, the magenta or purplish tones turn into a light blue similar to that of the outer portion of the petal.

Generally speaking, this new variety is especially useful as a garden plant, this being due to its prolific growth of panicles or bloom heads and of foliage, the latter completely covering the plant from the base to the flower cluster in many instances. The large number of panicles produced on each of the plants and their immense size somewhat hides the foliage, but its color, in contrast with the color of the flowers, greatly accentuates the delicacy of the flower coloring.

Other characteristics of the plant are illustrated in the colored photograph, such as symmetry of the panicles in relation to its supporting stem, glabrous stems and foliage, but the important distinctive characteristics of the plant over the known varieties are heretofore specifically described and also set forth in the appended claim.

Having now fully shown and described my new phlox and the mode of its production, what I claim and desire to secure by Letters Patent of the United States is:

A phlox as described and characterized by the hardy, vigorous, semi-dwarf plant; prolific growth, size and compactness of bloom heads; size and character of flowers; and flower color, which is principally a white having an overcast or hue of blue merging into a distinct blue flower center having a purplish tone.

JOHN J. GRULLEMANS.